United States Patent
Lim et al.

(12)

(10) Patent No.: US 6,887,280 B2
(45) Date of Patent: May 3, 2005

(54) HAIR COLORING COMPOSITIONS FOR USE IN OXIDATIVE HAIR DYEING

(75) Inventors: Mu-Ill Lim, Trumbull, CT (US); Yuh-Guo Pan, Stamford, CT (US); Sabina Burdzovic, Brooklyn, NY (US)

(73) Assignee: The Procter & Gamble Company, Cincinnati, OH (US)

( * ) Notice: Subject to any disclaimer, the term of this patent is extended or adjusted under 35 U.S.C. 154(b) by 178 days.

(21) Appl. No.: 10/090,377

(22) Filed: Mar. 4, 2002

(65) Prior Publication Data

US 2003/0196280 A1 Oct. 23, 2003

(51) Int. Cl.$^7$ .................................................. A61K 7/13
(52) U.S. Cl. .................. 8/405; 8/406; 8/408; 8/411; 8/568; 8/570; 8/573; 548/371.4; 548/371.7; 548/373.1; 546/251
(58) Field of Search .......................... 8/405, 406, 408, 8/411, 605, 602, 677, 568, 570, 573; 548/371.4, 371.7, 373.1; 546/251

(56) References Cited

U.S. PATENT DOCUMENTS

| 4,900,325 A | * | 2/1990 | Rose et al. ..................... 8/408 |
| 5,061,289 A | * | 10/1991 | Clausen et al. ................ 8/405 |
| 6,554,871 B2 | | 4/2003 | Braun .......................... 8/409 |

FOREIGN PATENT DOCUMENTS

| DE | 29909427 U | 7/1999 |
| DE | 10103160 A | 11/2001 |
| DE | 20206274 U | 8/2002 |

* cited by examiner

*Primary Examiner*—Margaret Einsmann
*Assistant Examiner*—Eisa Elhlio
(74) *Attorney, Agent, or Firm*—Marianne Dressman; Brian M. Bolam; Tara M. Rosnell

(57) ABSTRACT

Novel compositions for use in oxidative hair coloring compositions are provided. The compositions comprise one or more oxidative hair coloring N-aryl-m-phenyldiamine derivatives as couplers and one or more diaminopyrazole primary intermediates in combination.

18 Claims, No Drawings

HAIR COLORING COMPOSITIONS FOR USE IN OXIDATIVE HAIR DYEING

FIELD OF THE INVENTION

This invention relates to novel compositions for use in oxidative hair coloring comprising one or more oxidative hair coloring N-aryl-m-phenylenediamine derivatives as couplers and one or more diaminopyrazole primary intermediates in combination with one or more oxidizing agents. The invention also relates to use of these hair coloring compositions for the coloration or dyeing of hair.

BACKGROUND OF THE INVENTION

Coloration of hair is a procedure practiced from antiquity employing a variety of means. In modern times, the most extensively used method employed to color hair is to color hair by an oxidative dyeing process employing hair coloring systems utilizing one or more oxidative hair coloring agents in combination with one or more oxidizing agents.

Most commonly a peroxy oxidizing agent is used in combination with one or more oxidative hair coloring agents, generally small molecules capable of diffusing into hair and comprising one or more primary intermediates and one or more couplers. In this procedure, a peroxide material, such as hydrogen peroxide, is employed to activate the small molecules of primary intermediates so that they react with couplers to form larger sized compounds in the hair shaft to color the hair in a variety of shades and colors.

A wide variety of primary intermediates and couplers have been employed in such oxidative hair coloring systems and compositions. Among the primary intermediates employed there may be mentioned p-phenylenediamine, p-toluenediamine, p-aminophenol, 4-amino-3-methylphenol, and as couplers there may be mentioned resorcinol, 2-methylresorcinol, 3-aminophenol, and 5-amino-2-methylphenol. A majority of the shades have been produced with dyes based on p-phenylenediamine.

It is desirable that compositions used for the dyeing or coloration of hair be such as to provide overall color fastness of the dyed hair. Accordingly, the hair dyes with the compositions of the present invention should resist loss of color occasioned by washing, by acid perspiration, and by abrasion. Another desirable feature is that such compositions evidence color fastness evidence with minimal change of color in the blue direction due to the effect of acid perspiration. It is especially desirable that such compositions with such improved color fastness characteristics be available for dyeing or coloring hair purple, or to contribute chromophores in the purple spectrum to hair dye product compositions.

BRIEF SUMMARY OF THE INVENTION

This invention provides dyeing compositions comprising one or more N-aryl-m-phenylenediamine couplers of the formula (1):

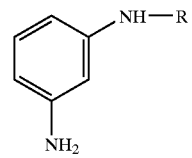

wherein R is a moiety selected from formulae (2), (3) or (4)

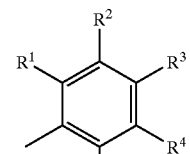

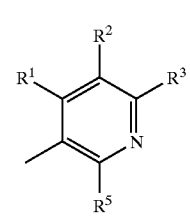

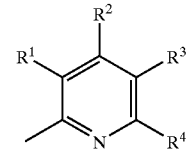

wherein $R^1$, $R^2$, $R^3$, $R^4$ and $R^5$ are each independently selected from a hydrogen atom, a halogen atom, a hydroxy group, an amino group, a $C_1$–$C_4$ alkyl or haloalkyl group, a $C_1$–$C_4$ alkoxy or haloalkoxy group, and a nitrile group, in combination with one or more diaminopyrazole primary intermediates of the formula (5):

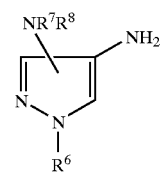

wherein $R^6$ and $R^7$ are the same or different and are selected from a hydrogen atom, a $C_1$ to $C_4$ alkyl group, a $C_2$ to $C_4$ hydroxyalkyl group, a benzyl group or a phenyl group, and $R^8$ is selected from a hydrogen atom, a $C_1$ to $C_4$ alkyl group, or a $C_2$ to $C_4$ hydroxyalkyl group, or the physiologically tolerated water soluble salts thereof.

These novel hair coloring compositions are used to provide coloration to hair in which there is good dye uptake by the hair and provides shades or colors which are stable over a relatively long period of time. The novel compositions provide for dyeing of hair to impart color or shades, especially purple, possessing good wash fastness, good selectivity, and do not undergo significant change on exposure to light, shampooing or acid perspiration. The dye compositions of the present invention are useful to provide purple chromophores to hair dye product composition, whereby the shade imparted to the hair dye with such product compositions may be adjusted.

DETAILED DESCRIPTION OF THE INVENTION

Preferred coupler compounds in the hair-coloring compositions of this invention are those of formula (1a)

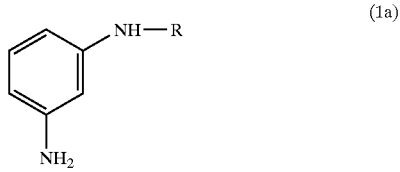

wherein R is a moiety of formula (2a)

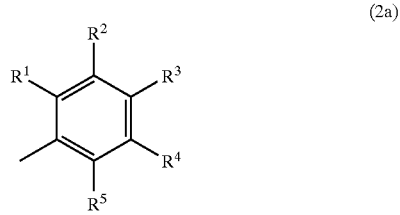

wherein $R^1$, $R^2$, $R^4$ and $R^5$ are hydrogen atoms and $R^3$ is selected from a hydrogen atom, a methyl group or a methoxy group, wherein $R^1$, $R^2$, $R^3$ and $R^5$ are hydrogen atoms and $R^4$ is selected from a methyl or methoxy group, or wherein $R^1$, $R^2$, $R^3$, $R^4$ and $R^5$ are all hydrogen atoms.

Preferred as a diaminopyrazole primary intermediate in the hair-coloring compositions of this invention is the compound 2-(4,5-diamino-pyrazol-1-yl)-ethanol, i.e., a compound of Formula 5 wherein $R^6$ is a hydroxyethyl group, $R^7$ and $R^8$ are each hydrogen atoms and the $NR^7R^8$ moiety is at the 5-position.

The coupler compounds of formula (1) of this invention are known, for example see U.S. Pat. No. 4,900,325 or are readily prepared according to the following reaction sequence where R is as defined hereinbefore.

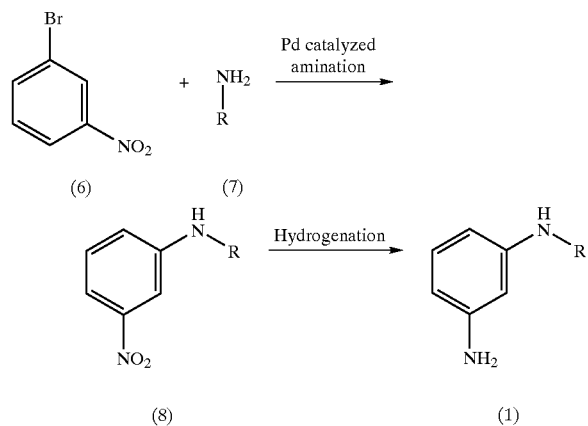

In this reaction 1-bromo-3-nitrobenzene (6) is subjected to palladium catalyzed amination with an aryl amine of the formula R—$NH_2$ (7) to produce an N-aryl-m-nitro-aminobenzene (8) that, when subjected to hydrogenation, produces an N-aryl-m-benzenediamine (1).

Using the above-described synthesis procedure the following two coupler compounds were prepared.

SYNTHESIS EXAMPLE 1

Synthesis of 4-methoxyphenyl-(3-amino-phenyl)-amine

A suspension of 1-bromo-3-nitrobenzene (6) (2 mmol, 0.40 g), p-methoxyaniline (7) (2.4 mmol, 0.30 g), sodium-tert-butoxide (2.8 mmol, 0.26 g), $Pd_2(dba)_3$ (10% mol, 0.18 g), BINAP (10% mol, 0.13 g) in toluene (4 mL, 0.5 M) was stirred for 18 h at 100° C.[1]. The mixture was cooled to room temperature, filtered on celite and washed with ethyl acetate (3×5 mL). The combined organic layer was washed with water (3×5 mL), dried with $Na_2SO_4$, evaporated, and purified (silica, 100% hexane) to give yellow-brownish powder (8) (0.1 g, 23% yield): $^1$H NMR (DMSO-$d_6$) δ 8.46 (s, 1H), 7.61 (t, 1H), 7.49 (d, 1H), 7.40 (t, 1H), 7.25 (d, 1H), 7.15 (d, 2H), 6.95 (d, 2H), 3.80 (s, 3H). Hydrogenation of (8) (0.1 g) with Pd/C (10%, 0.01 g) in MeOH (20 mL) for 2 h at 60 psi $H_2$ gave 4-methoxyphenyl-(3-amino-phenyl)-amine (1) (0.04 g, 45% yield): $^1$H NMR (DMSO-$d_6$) δ 7.51 (s, 1H), 7.00 (d, 2H), 6.82 (d, 3H), 6.20 (s, 1H), 6.12 (s, 1H), 5.99 (d, 1H), 4.48 (s, 2H), 3.75 (s, 3H); MS 214 ($M^+$), 199, 182, 169, 154, 107, 91, 85, 65.

1: R. A. Singer, J. P. Dadighi and S. L. Buchwald, J. Am. Chem. Soc. 1998, 120, 213.

SYNTHESIS EXAMPLE 2

Synthesis of 3-methoxyphenyl-(3-amino-phenyl)-amine

The compound 3-methoxyphenyl-(3-amino-phenyl)-amine was prepared according to the procedure described above of Synthesis Example 1 by substituting m-methoxyaniline for p-methoxyaniline as reactant (7). The product is characterized by the following parameters: $^1$H NMR (DMSO-$d_6$) δ 7.93 (s, 1H), 7.16 (d, 1H), 6.90 (t, 1H), 6.63 (d, 2H), 6.43 (t, 2H), 6.30 (d, 1H), 6.13 (d, 1H), 5.23 (s, 2H), 3.70 (s, 3H); MS 214 ($M^+$), 213, 198, 182, 169, 154, 143, 127, 107, 91, 85, 65.

The diaminopyrazole primary intermediates of formula (5) are either known or may be prepared by the processes described in U.S. Pat. No. 5,061,289, the disclosure of which is incorporated herein.

As used herein, the term "hair dyeing composition" (also synonymously referred to herein as the hair dye composition, the hair coloring composition, or the hair dye lotion) refers to the composition containing oxidation dyes, including the compounds described herein, prior to admixture with the developer composition. The term "developer composition" (also referred to as the oxidizing agent composition or the peroxide composition) refers to compositions containing an oxidizing agent prior to admixture with the hair dyeing composition. The term "hair dye product" or "hair dye system" (also referred to as the hair dyeing system, hair dyeing product, or hair coloring system) interchangeably refer to the combination of the hair dyeing composition and the developer composition before admixture, and may further include a conditioner product and instructions, such product or system often being provided packaged as a kit. The term "hair dyeing product composition" refers to the composition formed by mixing the hair dyeing composition and the developer composition. "Carrier" (or vehicle or base) refers to the combination of ingredients contained in a composition excluding the active agents (e.g., the oxidation hair dyes of the hair dyeing composition). Unless otherwise indicated all percentages are by weight unless other unit basis are indicated.

For hair coloring compositions of this invention, there may be used one or more of the N-aryl-m-phenylenediamine couplers in combination with one or more diaminopyrazole primary intermediates. The hair coloring compositions of this invention can also include one or more other primary intermediate compounds and/or one or more other coupler compounds, if so desired.

Suitable known primary intermediates include, for example:

p-phenylenediamine derivatives such as: benzene-1,4-diamine (commonly known as p-phenylenediamine), 2-methyl-benzene-1,4-diamine, 2-chlorobenzene-1,4-diamine, N-phenyl-benzene-1,4-diamine, N-(2-ethoxyethyl) benzene-1,4-diamine, 2-[(4-amino-phenyl)-(2-hydroxy-ethyl)-amino]-ethanol, (commonly known as N,N-bis(2-hydroxyethyl)-p-phenylenediamine)(2,5-diamino-phenyl)-methanol, 1-(2,5-diamino-phenyl)-ethanol, 2-(2,5-diamino-phenyl)-ethanol, N-(4-aminophenyl)benzene-1,4-diamine, 2,6-dimethyl-benzene-1,4-diamine, 2-isopropyl-benzene-1,4-diamine, 1-[(4-aminophenyl)amino]-propan-2-ol, 2-propyl-benzene-1,4-diamine, 1,3-bis[[(4-aminophenyl)(2-hydroxyethyl)amino]propan-2-ol, $N^4,N^4,2$-trimethylbenzene-1,4-diamine, 2-methoxy-benzene-1,4-diamine, 1-(2,5-diaminophenyl)ethane-1,2-diol, 2,3-dimethyl-benzene-1,4-diamine, N-(4-amino-3-hydroxy-phenyl)-acetamide, 2,6-diethylbenzene-1,4-diamine, 2,5-dimethylbenzene-1,4-diamine, 2-thien-2-ylbenzene-1,4-diamine, 2-thien-3-ylbenzene-1,4-diamine, 2-pyridin-3-ylbenzene-1,4-diamine, 1,1'-biphenyl-2,5-diamine, 2-(methoxymethyl)benzene-1,4-diamine, 2-(aminomethyl) benzene-1,4-diamine, 2-(2,5-diaminophenoxy)ethanol, N-[2-(2,5-diaminophenoxy)ethyl]-acetamide, N,N-dimethylbenzene-1,4-diamine, N,N-diethylbenzene-1,4-diamine, N,N-dipropylbenzene-1,4-diamine, 2-[(4-aminophenyl)(ethyl)amino]ethanol, 2-[(4-amino-3-methyl-phenyl)-(2-hydroxy-ethyl)-amino]ethanol, N-(2-methoxyethyl)-benzene-1,4-diamine, 3-[(4-aminophenyl) amino]propan-1-ol, 3-[(4-aminophenyl)-amino]propane-1,2-diol, N-{4-[(4-aminophenyl)amino]butyl}benzene-1,4-diamine, and 2-[2-(2-{2-[(2,5-diaminophenyl)oxy] ethoxy}ethoxy)ethoxy]benzene-1,4-diamine;

p-aminophenol derivatives such as: 4-amino-phenol (commonly known as p-aminophenol), 4-methylamino-phenol, 4-amino-3-methyl-phenol, 4-amino-2-hydroxymethyl-phenol, 4-amino-2-methyl-phenol, 4-amino-2-[(2-hydroxy-ethylamino)-methyl]-phenol, 4-amino-2-methoxymethyl-phenol, 5-amino-2-hydroxy-benzoic acid, 1-(5-amino-2-hydroxy-phenyl)-ethane-1,2-diol, 4-amino-2-(2-hydroxy-ethyl)-phenol, 4-amino-3-(hydroxymethyl)phenol, 4-amino-3-fluoro-phenol, 4-amino-2-(aminomethyl)-phenol, and 4-amino-2-fluoro-phenol;

o-aminophenol derivatives such as: 2-amino-phenol (commonly known as o-aminophenol), 2,4-diaminophenol, 2-amino-5-methyl-phenol, 2-amino-6-methyl-phenol, N-(4-amino-3-hydroxy-phenyl)-acetamide, and 2-amino-4-methyl-phenol; and heterocyclic derivatives such as: pyrimidine-2,4,5,6-tetramine (commonly known as 2,4,5,6-tetraaminopyridine), 1-methyl-1H-pyrazole-4,5-diamine, 2-(4,5-diamino-1H-pyrazol-1-yl)ethanol, $N^2,N^2$-dimethyl-pyridine-2,5-diamine, 2-[(3-amino-6-methoxypyridin-2-yl) amino]ethanol, 6-methoxy-$N^2$-methyl-pyridine-2,3-diamine, 2,5,6-triaminopyrimidin-4(1H)-one, pyridine-2,5-diamine, 1-isopropyl-1H-pyrazole-4,5-diamine, 1-(4-methylbenzyl)-1H-pyrazole-4,5-diamine, 1-(benzyl)-1H-pyrazole-4,5-diamine, and 1-(4-chlorobenzyl)-1H-pyrazole-4,5-diamine.

Suitable known couplers include, for example:

phenols, resorcinol and naphthol derivatives such as: naphthalene-1,7-diol, benzene-1,3-diol, 4-chlorobenzene-1,3-diol, naphthalen-1-ol, 2-methyl-naphthalen-1-ol, naphthalene-1,5-diol, naphthalene-2,7-diol, benzene-1,4-diol, 2-methyl-benzene-1,3-diol, 7-amino-4-hydroxy-naphthalene-2-sulfonic acid, 2-isopropyl-5-methylphenol, 1,2,3,4-tetrahydro-naphthalene-1,5-diol, 2-chloro-benzene-1,3-diol, 4-hydroxy-naphthalene-1-sulfonic acid, benzene-1,2,3-triol, naphthalene-2,3-diol, 5-dichloro-2-methylbenzene-1,3-diol, 4,6-dichlorobenzene-1,3-diol, and 2,3-dihydroxy-[1,4]naphthoquinone;

m-phenylenediamines such as: 2,4-diaminophenol, benzene-1,3-diamine, 2-(2,4-diamino-phenoxy)-ethanol, 2-[(3-amino-phenyl)-(2-hydroxy-ethyl)-amino]-ethanol, 2-mehyl-benzene-1,3-diamine, 2-[[2-(2,4-diamino-phenoxy)-ethyl]-(2-hydroxy-ethyl)-amino]-ethanol, 4-{3-[(2,4-diaminophenyl)oxy]propoxy}benzene-1,3-diamine, 2-(2,4-diamino-phenyl)-ethanol, 2-(3-amino-4-methoxy-phenylamino)-ethanol, 4-(2-amino-ethoxy)-benzene-1,3-diamine, (2,4-diamino-phenoxy)-acetic acid, 2-[2,4-diamino-5-(2-hydroxy-ethoxy)-phenoxy]-ethanol, 4-ethoxy-6-methyl-benzene-1,3-diamine, 2-(2,4-diamino-5-methyl-phenoxy)-ethanol, 4,6-dimethoxy-benzene-1,3-diamine, 2-[3-(2-hydroxy-ethylamino)-2-methyl-phenylamino]-ethanol, 3-(2,4-diamino-phenoxy)-propan-1-ol, N-[3-(dimethylamino)phenyl]urea, 4-methoxy-6-methylbenzene-1,3-diamine, 4-fluoro-6-methylbenzene-1,3-diamine, 2-({3-[(2-hydroxyethyl)amino]-4,6-dimethoxyphenyl}-amino)ethanol, 3-(2,4-diaminophenoxy)-propane-1,2-diol, 2-[2-amino-4-(methylamino)-phenoxy]ethanol, 2-[(5-amino-2-ethoxy-phenyl)-(2-hydroxy-ethyl)-amino]-ethanol, 2-[(3-aminophenyl)amino]ethanol, N-(2-aminoethyl)benzene-1,3-diamine, 4-{[(2,4-diamino-phenyl)oxy]methoxy}-benzene-1,3-diamine, and 2,4-dimethoxybenzene-1,3-diamine;

m-aminophenols such as: 3-amino-phenol, 2-(3-hydroxy-4-methyl-phenylamino)-acetamide, 2-(3-hydroxy-phenylamino)-acetamide, 5-amino-2-methyl-phenol, 5-(2-hydroxy-ethylamino)-2-methyl-phenol, 5-amino-2,4-dichloro-phenol, 3-amino-2-methyl-phenol, 3-amino-6-chloro-6-methyl-phenol, 5-amino-2-(2-hydroxy-ethoxy)-phenol, 2-chloro-5-(2,2,2-trifluoro-ethylamino)-phenol, 5-amino-4-chloro-2-methyl-phenol, 3-cyclopentylamino-phenol, 5-[(2-hydroxyethyl)amino]-4-methoxy-2-methylphenol, 5-amino-4-methoxy-2-methylphenol, 3-(dimethylamino)phenol, 3-(diethylamino)phenol, 5-amino-4-fluoro-2-methylphenol, 5-amino-4-ethoxy-2-methylphenol, 3-amino-2,4-dichloro-phenol, 3-[(2-methoxyethyl)amino]phenol, 3-[(2-hydroxyethyl)amino] phenol, 5-amino-2-ethyl-phenol, 5-amino-2-methoxyphenol, 5-[(3-hydroxypropyl)amino]-2-methylphenol, 3-[(3-hydroxy-2-methylphenyl)-amino] propane-1,2-diol, and 3-[(2-hydroxyethyl)amino]-2-methylphenol; and heterocyclic derivatives such as: 3,4-dihydro-2H-1,4-benzoxazin-6-ol, 4-methyl-2-phenyl-2,4-dihydro-3H-pyrazol-3-one, 6-methoxyquinolin-8-amine, 4-methylpyridine-2,6-diol, 2,3-dihydro-1,4-benzodioxin-5-ol, 1,3-benzodioxol-5-ol, 2-(1,3-benzodioxol-5-ylamino) ethanol, 3,4-dimethylpyridine-2,6-diol, 5-chloropyridine-2,3-diol, 2,6-dimethoxypyridine-3,5-diamine, 1,3-benzodioxol-5-amine, 2-{[3,5-diamino-6-(2-hydroxy-ethoxy)-pyridin-2-yl]oxy}-ethanol, 1H-indol-4-ol, 5-amino-2,6-dimethoxypyridin-3-ol, 1H-indole-5,6-diol, 1H-indol-7-ol, 1H-indol-5-ol, 1H-indol-6-ol, 6-bromo-1,3-benzodioxol- 5-ol, 2-aminopyridin-3-ol, pyridine-2,6-diamine, 3-[(3,5-diaminopyridin-2-yl)oxy]propane-1,2-diol, 5-[(3,5-diaminopyridin-2-yl)oxy]pentane-1,3-diol, 1H-indole-2,3-dione, indoline-5,6-diol, 3,5-dimethoxypyridine-2,6-diamine, 6-methoxypyridine-2,3-diamine, and 3,4-dihydro-2H-1,4-benzoxazin-6-amine.

Preferred primary intermediates include:

p-phenylenediamine derivatives such as: 2-methyl-benzene-1,4-diamine, benzene-1,4-diamine, 1-(2,5-diamino-phenyl)-ethanol, 2-(2,5-diamino-phenyl)-ethanol, N-(2-methoxyethyl)benzene-1,4-diamine, 2-[(4-amino-phenyl)-(2-hydroxy-ethyl)-amino]-ethanol, and 1-(2,5-diaminophenyl)ethane-1,2-diol;

p-aminophenol derivatives such as 4-amino-phenol, 4-methylamino-phenol, 4-amino-3-methyl-phenol, 4-amino-2-methoxymethyl-phenol, and 1-(5-amino-2-hydroxy-phenyl)-ethane-1,2-diol;

o-aminophenol derivatives such as: 2-amino-phenol, 2-amino-5-methyl-phenol, 2-amino-6-methyl-phenol, N-(4-amino-3-hydroxy-phenyl)-acetamide, and 2-amino-4-methyl-phenol; and heterocyclic derivatives such as: pyrimidine-2,4,5,6-tetramine, 1-methyl-1H-pyrazole-4,5-diamine, 2-(4,5-diamino-1H-pyrazol-1-yl)ethanol, 1-(4-methylbenzyl)-1H-pyrazole-4,5-diamine, 1-(benzyl)-1H-pyrazole-4,5-diamine, and $N^2,N^2$-dimethyl-pyridine-2,5-diamine.

Preferred couplers include:

phenols, resorcinol and naphthol derivatives such as: naphthalene-1,7-diol, benzene-1,3-diol, 4-chlorobenzene-1,3-diol, naphthalen-1-ol, 2-methyl-naphthalen-1-ol, naphthalene-1,5-diol, naphthalene-2,7-diol, benzene-1,4-diol, 2-methyl-benzene-1,3-diol, and 2-isopropyl-5-methylphenol;

m-phenylenediamines such as: benzene-1,3-diamine, 2-(2,4-diamino-phenoxy)-ethanol, 4-{3-[(2,4-diaminophenyl)oxy]propoxy}benzene-1,3-diamine, 2-(3-amino-4-methoxy-phenylamino)-ethanol, 2-[2,4-diamino-5-(2-hydroxy-ethoxy)-phenoxy]-ethanol, and 3-(2,4-diamino-phenoxy)-propan-1-ol;

m-aminophenols such as: 3-amino-phenol, 5-amino-2-methyl-phenol, 5-(2-hydroxy-ethylamino)-2-methyl-phenol, and 3-amino-2-methyl-phenol; and heterocyclic derivatives such as: 3,4-dihydro-2H-1,4-benzoxazin-6-ol, 4-methyl-2-phenyl-2,4-dihydro-3H-pyrazol-3-one, 1,3-benzodioxol-5-ol, 1,3-benzodioxol-5-amine, 1H-indol-4-ol, 1H-indole-5,6-diol, 1H-indol-7-ol, 1H-indol-5-ol, 1H-indol-6-ol, 1H-indole-2,3-dione, pyridine-2,6-diamine, and 2-aminopyridin-3-ol.

Most preferred primary intermediates include:

p-phenylenediamine derivatives such as: 2-methyl-benzene-1,4-diamine, benzene-1,4-diamine, 2-(2,5-diamino-phenyl)-ethanol, 1-(2,5-diamino-phenyl)-ethanol, and 2-[(4-amino-phenyl)-(2-hydroxy-ethyl)-amino]-ethanol;

p-aminophenol derivatives such as: 4-amino-phenol, 4-methylamino-phenol, 4-amino-3-methyl-phenol, and 1-(5-amino-2-hydroxy-phenyl)-ethane-1,2-diol;

o-aminophenols such as: 2-amino-phenol, 2-amino-5-methyl-phenol, 2-amino-6-methyl-phenol, and N-(4-amino-3-hydroxy-phenyl)-acetamide; and heterocyclic derivatives such as: pyrimidine-2,4,5,6-tetramine, 2-(4,5-diamino-1H-pyrazol-1-yl)ethanol, 1-(4-methylbenzyl)-1H-pyrazole-4,5-diamine, and 1-(benzyl)-1H-pyrazole-4,5-diamine.

Most preferred couplers include:

phenols, resorcinol and naphthol derivatives such as: benzene-1,3-diol, 4-chlorobenzene-1,3-diol, naphthalen-1-ol, 2-methyl-naphthalen-1-ol, and 2-methyl-benzene-1,3-diol;

m-phenylenediamine such as: 2-(2,4-diamino-phenoxy)-ethanol, 2-(3-amino-4-methoxy-phenylamino)-ethanol, 2-[2,4-diamino-5-(2-hydroxy-ethoxy)-phenoxy]-ethanol, and 3-(2,4-diamino-phenoxy)-propan-1-ol;

m-aminophenols such as: 3-amino-phenol, 5-amino-2-methyl-phenol, 5-(2-hydroxy-ethylamino)-2-methyl-phenol, and 3-amino-2-methyl-phenol; and heterocyclic derivatives such as: 3,4-dihydro-2H-1,4-benzoxazin-6-ol, 4-methyl-2-phenyl-2,4-dihydro-3H-pyrazol-3-one, 1H-indol-6-ol, and 2-aminopyridin-3-ol.

Understandably, the coupler compounds and the primary intermediate compounds, including the compounds (1) and (5) of this invention, in so far as they are bases, can be used as free bases or in the form of their physiologically compatible salts with organic or inorganic acids, such as hydrochloric, citric, acetic, tartaric, or sulfuric acids, or, in so far as they have aromatic OH groups, in the form of their salts with bases, such as alkali phenolates.

The total amount of dye precursors (e.g., primary intermediate and coupler compounds, including the compounds of this invention) in the hair dyeing compositions of this invention is generally from about 0.002 to about 20, preferably from about 0.04 to about 10, and most preferably from about 0.1 to about 7.0 weight percent, based on the total weight of the hair dyeing composition. The primary intermediate and coupler compounds are generally used in molar equivalent amounts. However, it is possible to use the primary intermediate compounds in either excess or deficiency, i.e., a molar ratio of primary intermediate to coupler generally ranging from about 5:1 to about 1:5.

The hair dyeing compositions of this invention will contain the primary intermediate and coupler combination of this invention in an effective dyeing amount, each of the primary intermediate and coupler being generally in an amount of from about 0.001 to about 10 weight percent by weight of the hair dye composition, preferably from about 0.01 to about 5.0 weight percent. Other couplers, when present, are typically present in an amount such that in aggregate the concentration of couplers in the composition is from about 0.002 to about 10 weight percent, preferably from about 0.01 to about 5.0 weight percent. Other primary intermediates when present are present in an effective dyeing concentration, generally an amount of from about 0.001 to about 10.0 weight percent by weight of the hair dye composition, preferably from about 0.01 to about 5.0 weight percent. The remainder of the hair dye composition comprises a carrier or vehicle for the couplers and primary intermediates, and comprises various adjuvants as described below.

Any suitable carrier or vehicle, generally an aqueous or hydroalcoholic solution, can be employed, preferably an aqueous solution. The carrier or vehicle will generally comprise more than 80 weight percent of the hair dye composition, typically 90 to 99 weight percent, preferably 94 to 99 weight percent. The hair coloring compositions of this invention may contain as adjuvants one or more cationic, anionic, amphoteric, or zwitterionic surface active agents, perfumes, antioxidants such as ascorbic acid, thioglycolic acid or sodium sulfite, chelating and sequestering agents such as EDTA, thickening agents, alkalizing or acidifying agents, solvents, diluents, inerts, dispersing agents, penetrating agents, defoamers, enzymes, and other dye agents (e.g., synthetic direct and natural dyes). These adjuvants are cosmetic additive ingredients commonly used in compositions for coloring hair.

The hair dye compositions of the present invention are used by admixing them with a suitable oxidant, which reacts with the hair dye precursors to develop the hair dye. Any suitable oxidizing agent can be employed in the hair dye product compositions of this invention, particularly hydrogen peroxide ($H_2O_2$) or precursors therefor. Also suitable are urea peroxide, the alkali metal salts of persulfate, perborate, and percarbonate, especially the sodium salt, and melamine peroxide. The oxidant is usually provided in an aqueous composition generally referred to as the developer composition, which normally is provided as a separate component of the finished hair dye product and present in a separate container. The developer composition may also contain, to the extent compatible, various ingredients needed to form the developer composition, i.e., peroxide stabilizers, foam formers, etc., and may incorporate one or more of the adjuvants referred to above, e.g., surface active agents, thickeners, pH modifiers, etc. Upon mixing the hair coloring composition and the developer composition to form a hair dye product composition, the adjuvants are provided in the hair dye product composition as it is applied to the hair to achieve desired product attributes, e.g., pH, viscosity, rheology, etc.

The form of the hair dye product compositions according to the invention can be, for example, a solution, especially an aqueous or aqueous-alcoholic solution. However, the form that is preferred is a thick liquid, cream, gel or an emulsion whose composition is a mixture of the dye ingredients with the conventional cosmetic additive ingredients suitable for the particular preparation.

Suitable conventional cosmetic additive ingredients useful in the hair dye and developer compositions, and hence in the hair dye product compositions of this invention are described below, and may be used to obtain desired characteristics of the hair dye, developer and hair dye product compositions.

Solvents: In addition to water, solvents that can be used are lower alkanols (e.g., ethanol, propanol, isopropanol, benzyl alcohol); polyols (e.g., carbitols, propylene glycol, hexylene glycol, glycerin). See WO 98/27941 (section on diluents) incorporated by reference. See also U.S. Pat. No. 6,027,538 incorporated by reference. Under suitable processing, higher alcohols, such as C8 to C18 fatty alcohols, especially cetyl alcohol, are suitable organic solvents, provided they are first liquified by melting, typically at low temperature (50 to 80° C.), before incorporation of other, usually lipophilic, materials.

The organic solvents are typically present in the hair dye compositions in an amount of from about 5 to about 30% by weight of the hair dye composition. Water is usually present in an amount of from about 5 to about 90% by weight of the hair dye composition, preferably from about 15 to about 75% by weight and most preferably from about 30 to about 65% by weight.

Surfactants: These materials are from the classes of anionic, cationic, amphoteric (including zwitterionic surfactants) or nonionic surfactant compounds. (Cationic surfactants, generally included as hair conditioning materials, are considered separately below.) Suitable surfactants, other than cationic surfactants, include fatty alcohol sulfates, ethoxylated fatty alcohol sulfates, alkylsulfonates, alkylbenzensulfonates, alkyltrimethylammonium salts, alkylbetaines, ethoxylated fatty alcohols, ethoxylated fatty acids, ethoxylated alkylphenols, block polymers of ethylene and/or propylene glycol, glycerol esters, phosphate esters, fatty acid alkanol amides and ethoxylated fatty acid esters, alkyl sulfates, ethoxylated alkyl sulfates, alkyl glyceryl ether sulfonates, methyl acyl taurates, acyl isethionates, alkyl ethoxy carboxylates, fatty acid mono- and diethanolamides. Especially useful are sodium and ammonium alkyl sulfates, sodium and ammonium ether sulfates having 1 to 3 ethylene oxide groups, and nonionic surfactants sold as Tergitols, e.g., C11–C15 Pareth-9, and Neodols, e.g., C12–C15 Pareth-3. They are included for various reasons, e.g., to assist in thickening, for forming emulsions, to help in wetting hair during application of the hair dye product composition, etc. Amphoteric surfactants include, for example, the asparagine derivatives as well betaines, sultaines, glycinates and propionates having an alkyl or alkylamido group of from about 10 to about 20 carbon atoms. Typical amphoteric surfactants suitable for use in this invention include lauryl betaine, lauroamphoglycinate, lauroamphopropionate, lauryl sultaine, myristamidopropyl betaine, myristyl betaine, stearoamphopropylsulfonate, cocamidoethyl betaine, cocamidopropyl betaine, cocoamphoglycinate, cocoamphocarboxypropionate, cocoamphocarboxyglycinate, cocobetaine, and cocoamphopropionate. Reference is made to WO 98/52523 published Nov. 26, 1998 and WO 01/62221 published Aug. 30, 2001, both incorporated herein by reference thereto.

The amount of surfactants in the hair dye compositions is normally from about 0.1% to 30% by weight, preferably 1% to 15% by weight.

Thickeners: Suitable thickeners include such as higher fatty alcohols, starches, cellulose derivatives, petrolatum, paraffin oil, fatty acids and anionic and nonionic polymeric thickeners based on polyacrylic and polyurethane polymers. Examples are hydroxyethyl cellulose, hydroxymethylcellulose and other cellulose derivatives, hydrophobically modified anionic polymers and nonionic polymers, particularly such polymers having both hydrophilic and hydrophobic moieties (i.e., amphiphilic polymers). Useful nonionic polymers include polyurethane derivatives such as PEG-150/stearyl alcohol/SDMI copolymer. Suitable polyether urethanes are Aculyn® 22, 44 and Aculyne® 46 polymers sold by Rohm & Haas. Other useful amphiphilic polymers are disclosed in U.S. Pat. No. 6,010,541 incorporated by reference. See also WO 01/62221 mentioned above. Examples of anionic polymers that can be used as thickeners are acrylates copolymer, acrylates/ceteth-20 methacrylates copolymer, acrylates/ceteth-20 itaconate copolymer, and acrylates/beheneth-25 acrylates copolymers. In the case of the associative type of thickeners, e.g., Aculyns 22, 44 and 46, the polymer may be included in one of either the hair dye composition or the developer composition of the hair dye product and the surfactant material in the another. Thus, upon mixing of the hair dye and developer compositions, the requisite viscosity is obtained. The thickeners are provided in an amount to provide a suitably thick product as it is applied to the hair. Such products generally have a viscosity of from 1000 to 100000 cps, and often have a thixotropic rheology.

pH Modifying agents: Suitable materials that are used to adjust pH of the hair dye compositions include alkalizers such alkali metal and ammonium hydroxides and carbonates, especially sodium hydroxide and ammonium carbonate, ammonia, organic amines including methylethanolamine, aminomethylpropanol, mono-, di-, and triethanolamine, and acidulents such as inorganic and inorganic acids, for example phosphoric acid, acetic acid, ascorbic acid, citric acid or tartaric acid, hydrochloric acid, etc. See U.S. Pat. No. 6,027,538 incorporated by reference.

Conditioners: Suitable materials include silicones and silicone derivatives; hydrocarbon oils; monomeric quaternary compounds, and quaternized polymers. Monomeric quaternary compounds are typically cationic compounds, but may also include betaines and other amphoteric and zwitterionic materials that provide a conditioning effect. Suitable monomeric quaternary compounds include behentrialkonium chloride, behentrimonium chloride, benzalkonium bromide or chloride, benzyl triethyl ammonium chloride, bis-hydroxyethyl tallowmonium chloride, C12–18 dialkyldimonium chloride, cetalkonium chloride, ceteartrimonium bromide and chloride, cetrimonium bromide, chloride and methosulfate, cetylpyridonium chloride, cocamidoproypl ethyldimonium ethosulfate, cocamidopropyl ethosulfate, cocoethyldimonium ethosulfate, cocotrimonium chloride and ethosulfate, dibehenyl dimonium chloride, dicetyldimonium chloride, dicocodimonium chloride, dilauryl dimonium chloride, disoydimonium chloride, ditallowdimonium chloride, hydrogenated tallow trimonium chloride, hydroxyethyl cetyl dimonium chloride, myristalkonium chloride, olealkonium chloride, soyethomonium ethosulfate, soytrimonium chloride, stearalkonium chloride, and many other compounds. See WO 98/27941 incorporated by reference. Quaternized polymers are typically cationic polymers, but may also include amphoteric and zwitterionic polymers. Useful polymers are exemplified by polyquaternium-4, polyquaternium-6, polyquaternium-7, polyquaternium-8, polyquaternium-9, polyquaternium-10, polyquaternium-22, polyquaternium-32, polyquaternium-39, polyquaternium-44 and polyquaternium-47. Silicones suitable to condition hair are dimethicone, amodimethicone, dimethicone copolyol and dimethiconol. See also WO 99/34770 published Jul. 15, 1999, incorporated by reference, for suitable silicones. Suitable hydrocarbon oils would include mineral oil.

Conditioners are usually present in the hair dye composition in an amount of from about 0.01 to about 5% by weight of the composition.

Direct Dyes: The hair dyeing compositions according to the invention can also contain compatible direct dyes including Disperse Black 9, HC Yellow 2, HC Yellow 4, HC Yellow 15, 4-nitro-o-phenylenediamine, 2-amino-6-chloro-4-nitrophenol, HC Red 3, Disperse Violet 1, HC Blue 2, Disperse Blue 3, and Disperse Blue 377. These direct dyes can be contained in the hair coloring compositions of the invention in an amount of from about 0.05 to 4.0 percent by weight.

Natural ingredients: For example, proteins and protein derivatives, and plant materials such as aloe, chamomile and henna extracts.

Other adjuvants include polysaccharides, alkylpolyglycosides, buffers, chelating and sequestrant agents, antioxidants, and peroxide stabilizing agents as mentioned in WO 01/62221, etc.

The adjuvants referred to above but not specifically identified that are suitable are listed in the International Cosmetics Ingredient Dictionary and Handbook, (Eighth Edition) published by The Cosmetics, Toiletry, and Fragrance Association, incorporated by reference. In particular reference is made to Volume 2, Section 3 (Chemical Classes) and Section 4 (Functions) are useful in identifying a specific adjuvant to achieve a particular purpose or multipurpose.

The above-mentioned conventional cosmetic ingredients are used in amounts suitable for their functional purposes. For example, the surfactants used as wetting agents, associative agents, and emulsifiers are generally present in concentrations of from about 0.1 to 30 percent by weight, the thickeners are useful in an amount of from about 0.1 to 25 percent by weight, and the hair care functional materials are typically used in concentrations of from about 0.01 to 5.0 percent by weight.

The hair dyeing product composition as it is applied to the hair, i.e., after mixing the hair dye composition according to the invention and the developer, can be weakly acidic, neutral or alkaline according to their composition. The hair dye compositions can have pH values of from about 6 to 11.5, preferably from about 6.8 to about 10, and especially from about 8 to about 10. The pH of the developer composition is typically acidic, and generally the pH is from about 2.5 to about 6.5, usually about 3 to 5. The pH of the hair dye and developer compositions is adjusted using a pH modifier as mentioned above.

In order to use the hair coloring composition for dyeing hair, the above-described hair coloring compositions according to the invention are mixed with an oxidizing agent immediately prior to use and a sufficient amount of the mixture is applied to the hair, according to the hair abundance, generally from about 60 to 200 grams. Some of the adjuvants listed above (e.g., thickeners, conditioners, etc.) can be provided in the dye composition or the developer, or both, depending on the nature of the ingredients, possible interactions, etc., as is well known in the art.

Typically, hydrogen peroxide, or its addition compounds with urea, melamine, sodium borate or sodium carbonate, can be used in the form of a 3 to 12 percent, preferably 6 percent, aqueous solution as the oxidizing agent for developing the hair dye. If a 6 percent hydrogen peroxide solution is used as oxidizing agent, the weight ratio of hair coloring composition to the developer composition is 5:1 to 1:5, but preferably 1:1. In general, the hair dyeing composition comprising primary intermediate(s) and coupler(s) is prepared and at the time of use is admixed with the developer composition containing the oxidizing agent to obtain an essentially homogenous, preferably thickened, composition (the hair dye product composition). Upon such preparation the hair dye product composition is applied to the hair to be dyed and remains in contact with the hair for an amount of time effective to dye the hair. The hair dye product composition is allowed to act on the hair for about 2 to about 60 minutes, preferably about 15 to 45, especially about 30 minutes, at about 15 to 50° C. Thereafter, the hair is rinsed with water, to remove the hair dye product composition and dried. If necessary, the hair is washed with a shampoo and rinsed, e.g., with water or a weakly acidic solution, such as a citric acid or tartaric acid solution, and dried. Optionally, a separate conditioning product may also be provided.

Together, the hair dye composition and the developer composition form a system for dyeing hair. This system may be provided as a kit comprising in a single package separate containers of the hair dye composition, the developer, the optional conditioner or other hair treatment product, and instructions for use.

Especially useful primary intermediate and coupler combinations of this invention will provide coloring compositions having outstanding color fastness, fastness to washing, fastness to rubbing, and good selectivity.

It has surprisingly been discovered that when N-phenyl-benzene-1,3-diamine couples with 2-(4,5-diamino-pyrazole-1-yl)-ethanol to color Piedmont hair the hair is colored purple, whereas coupling of N-methyl-benzene-1,3-diamine or benzene-1,3-diamine with the same pyrazole primary intermediate dyes the hair red-purple and red, respectively.

The advantageous properties of the hair-coloring compositions of this invention compared to closely related hair-coloring composition are illustrated by the following tests.

DYEING EXAMPLE 1

The following composition shown in Table 1 can be used for dyeing Piedmont hair. 100 g of the dyeing composition is mixed with 100 g 20 volume hydrogen peroxide. The resulting mixture is applied to the hair and permitted to remain in contact with the hair for 30 minutes. The dyed hair is then shampooed, rinsed with water and dried. The ranges of ingredients set out in Table 1 are illustrative of useful concentrations of the recited materials in a hair dye product.

TABLE 1

Composition for Dyeing Hair

| Ingredients | Range (wt %) | Weight (%) |
|---|---|---|
| Cocamidopropyl betaine | 0–25 | 17.00 |
| Polyquaternium-22 | 0–7 | 5.00 |
| Monoethanolamine[1] | 0–15 | 2.00 |
| Oleic Acid | 2–22 | 0.75 |
| Citric Acid | 0–3 | 0.10 |
| 28% Ammonium hydroxide[1] | 0–15 | 5.00 |
| Behentrimonium chloride | 1–5 | 0.50 |
| Sodium sulfite | 0–1 | 0.10 |
| EDTA | 0–1 | 0.10 |
| Erythorbic acid | 0–1 | 0.40 |
| Ethoxydiglycol | 1–10 | 3.50 |
| C11-15 Pareth-9 (Tergitol 15-S-9) | 0.5–5 | 1.00 |
| C12-15 Pareth-3 (Neodol 25-3) | 0.25–5 | 0.50 |
| Isopropanol | 2–10 | 4.00 |
| Propylene glycol | 1–12 | 2.00 |
| p-Phenylenediamine | 0–5 | 2 mmoles |
| N,N-Bis(hydroxyethyl)-p-phenylene diamine | 0–5 | 2 mmoles |
| 3-Methyl-p-aminophenol | 0–5 | 1 mmoles |
| p-Aminophenol | 0–5 | 1 mmoles |
| Primary intermediate of this invention | 0.5–5 | 3 mmoles |
| Coupler of this invention | 0.5–5 | 3 mmoles |
| 5-Amino-2-Methyl Phenol | 0–5 | 3 mmoles |
| 2,4-Diaminophenoxyethanol | 0–5 | 3 mmoles |
| m-Phenylenediamine | 0–5 | 1 mmoles |
| Water | qs to 100.00 | qs to 100.00 |

[1]In the aggregate, these ingredients are in the range of 2 to 15% by weight.

DYEING EXAMPLE 2

Piedmont hair weighing from 700 to 900 mg was used. The following compositions A (of this invention), B (comparative) and C (comparative) shown in Table 2 were used for dyeing Piedmont hair. 100 g of hair dyeing composition was mixed with 100 g of 20 volume hydrogen peroxide. The resulting mixture was applied to the hair and permitted to remain in contact with hair for 30 minutes at about 20° C. Thus dyed hair was then shampooed and rinsed with water and dried. Minolta spectrophotometer CM-3700d from Minolta Co. is used. Color space is CIE L*a*b* and illuminant is D65 daylight with 10° observer. The color space L* indicates lightness and a* and b* are the chromaticity coordinates. +a is the red direction, −a is the green direction, +b is the yellow direction, and −b is the blue direction. Overall color change is represented by ΔE where ΔE is defined by the following formula.

$$\Delta E = \sqrt{(\Delta L^*)^2 + (\Delta a^*)^2 + (\Delta b^*)^2}$$

Acid Perspiration Test Procedure

A dyed tress was placed in a jar containing 60 ml of acid perspiration solution described below and left for 18 h at 40° C. The tress was then rinsed, dried, and measured by Minolta CM-3700d to obtain CIE L*a*b*. The process was repeated under the same conditions in a freshly prepared solution for another 18 h and the tress was again rinsed, dried, and measured.

Acid Perspiration solution consists of 10 g sodium chloride, 1 g lactic acid (USP 85%), 1 g anhydrous disodium hydrogen phosphate ($Na_2HPO_4$) and 0.25 g (+) histidine monohydrochloride in 1 L distilled water.

TABLE 2

| Hair Dye Composition | A (%) | B (%) | C (%) |
|---|---|---|---|
| Cocamidopropyl betaine | 17.00 | 17.00 | 17.00 |
| Ethanolamine | 2 | 2 | 2 |
| Oleic Acid | 0.75 | 0.75 | 0.75 |
| Citric Acid | 0.1 | 0.1 | 0.1 |
| Ammonium hydroxide | 5.0 | 5.0 | 5.0 |
| Behentrimonium chloride | 0.5 | 0.5 | 0.5 |
| Sodium sulfite | 0.1 | 0.1 | 0.1 |
| EDTA | 0.1 | 0.1 | 0.1 |
| Erythorbic acid | 0.4 | 0.4 | 0.4 |
| N-(2-Hydroxyethyl)-4,5-diaminopyrazole sulfate | 0.24 | 0.24 | 0.24 |
| N-Phenyl-benzene-1,3-diamine | 0.461 | | |
| N-Methyl-benzene-1,3-diamine | | 0.305 | |
| Benzene-1,3-diamine | | | 0.27 |
| Water | QS 100 | QS 100 | QS 100 |
| Shade on Piedmont hair | Purple | Dark Red | Red |

TABLE 3

The CIE L*a*b* values obtained from Compositions A, B, and C

| | Before acid perspiration | | | After acid perspiration | | | |
|---|---|---|---|---|---|---|---|
| Composition | L* | a* | b* | L* | a* | b* | ΔE |
| A | 34.03 | 17.73 | −16.75 | 39.00 | 16.96 | −13.94 | 5.76 |
| B | 25.42 | 28.52 | −3.49 | 48.97 | 19.05 | 1.47 | 25.87 |
| C | 27.53 | 32.42 | −4.93 | 48.01 | 23.12 | −0.45 | 22.93 |

Surprisingly, N-phenyl-benzene-1,3-diamine couples with 2-(4,5-diamino-pyrazol-1-yl)-ethanol to color the Piedmont hair purple (Composition A), while coupling of N-methyl-benzene-1,3-diamine (Composition B) or benzene-1,3-diamine (Composition C) with the same pyrazole primary intermediate dyes the hair dark red and red, respectively. Additionally, the −b* value of Composition A is −16.75 in contrast to −b* values of −3.49 and −4.93 for Compositions B and C, respectively.

Per Table 3, the fastness of the dyed hair to the effect of acid perspiration shows that Composition A containing N-phenyl-benzene-1,3-diamine exhibits much better color fastness than Composition B containing N-methyl-benzene-1,3-diamine or Composition C containing benzene-1,3-diamine. After 36 hours testing, the total color difference (ΔE) of Composition A is only 5.76 whereas the ΔE for Composition B and Composition C is 25.87 and 22.93, respectively.

Exemplary combinations of hair coloring components comprising the novel and diaminopyrazole/N-aryl-m-phenylenediamine combination of the present invention in further combination with one or more conventional oxidative hair dye primary intermediates and/or couplers are shown in combinations C1 to C81 in Tables A through E. Reading down the columns in Tables A through E, the Xes designate the dye compounds (including the primary intermediates and couplers of the instant invention) that form illustratively suitable combinations of dyes that can be formulated according to the present invention. For example, in Combination No. C1 in Column 4 of Table A, a coupler of Formula 1 of this invention and a primary intermediate of Formula 5 of this invention, wherein R, $R^1$, $R^2$, $R^3$, $R^4$, $R^5$, $R^6$, $R^7$, and $R^8$ are as defined hereinbefore, can be combined with 2-amino-phenol. The N-aryl-m-phenylenediamine coupler is the first compound identified in the tables, and the diaminopyrazole primary intermediate is the last compound identified in the tables. These combinations of hair dye components can be used with any suitable base or vehicle, e.g., the base identified in Table 1.

With the foregoing description of the invention, those skilled in the art will appreciate that modifications may be made to the invention without departing from the spirit thereof. Therefore, it is not intended that the scope of the invention be limited to the specific embodiments illustrated and described.

TABLE A

| Structure | IUPAC Name | Name | C1 | C2 | C3 | C4 | C5 | C6 | C7 | C8 | C9 | C10 | C11 |
|---|---|---|---|---|---|---|---|---|---|---|---|---|---|
| (m-phenylenediamine with NHR) | | | X | X | X | X | X | X | X | X | X | X | X |
| (2-methyl-1,4-diaminobenzene) | 2-Methyl-benzene-1,4-diamine | p-Toluene-diamine | | | | | | | | | | X | X |
| (1,4-diaminobenzene) | Benzene-1,4-diamine | p-Phenylene-diamine | | | | | | | | | | | |
| (4-amino-N,N-bis(2-hydroxyethyl)aniline) | 2-[(4-Amino-phenyl)-(2-hydroxy-ethyl)-amino]-ethanol | N,N-Bis(2-hydroxy-ethyl)-p-phenylene-diamine | | | | | | | | | | | |
| (4-aminophenol) | 4-Amino-phenol | p-Aminophenol | | | | | | | | | | | |
| (4-amino-3-methylphenol) | 4-Amino-3-methyl-phenol | 3-Methyl-p-aminophenol | | | | | | | | | | | |
| (2-aminophenol) | 2-Amino-phenol | o-Aminophenol | X | | | | | | | | X | | |
| (resorcinol) | Benzene-1,3-diol | Resorcinol | | X | | | | | | | | | X |
| (2-methylresorcinol) | 2-Methyl-benzene-1,3-diol | 2-Methyl-resorcinol | | | X | | | | | | | | |

TABLE A-continued

Dye Combinations

| Structure | IUPAC Name | Name | C1 | C2 | C3 | C4 | C5 | C6 | C7 | C8 | C9 | C10 | C11 |
|---|---|---|---|---|---|---|---|---|---|---|---|---|---|
| 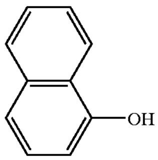 | Naphthalen-1-ol | 1-Naphthol | | | | X | | | | | | | |
| 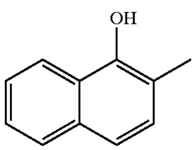 | 2-Methyl-naphthalen-1-ol | 2-Methyl-1-naphthol | | | | | X | | | | | | |
| 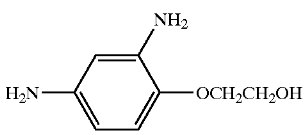 | 2-(2,4-Diamino-phenoxy)-ethanol | 2,4-Diamino-phenoxyethanol | | | | | | X | | | | | |
| 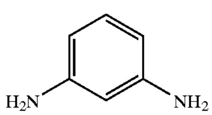 | Benzene-1,3-diamine | m-Phenylenediamine | | | | | | | X | | | | |
| 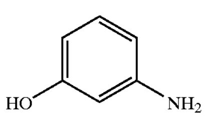 | 3-Amino-phenol | m-Aminophenol | | | | | | | | X | | | |
| 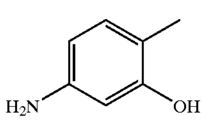 | 5-Amino-2-methyl-phenol | 2-Hydroxy-4-aminotoluene | | | | | | | | | X | | |
| 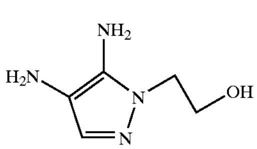 | 2-(4,5-Diamino-pyrazol-1-yl)-ethanol | 1-Hydroxyethyl-4,5-diamino-pyrazole | X | X | X | X | X | X | X | X | X | X | X |

TABLE B
Dye Combinations
| Structure | C12 | C13 | C14 | C15 | C16 | C17 | C18 | C19 | C20 | C21 | C22 | C23 | C24 | C25 | C26 | C27 | C28 | C29 |
|---|---|---|---|---|---|---|---|---|---|---|---|---|---|---|---|---|---|---|
|  | x | x | x | x | x | x | x | x | x | x | x | x | x | x | x | x | x | x |
|  | x | x | x | x | x | x | x | | | | | | | | | | | |
| 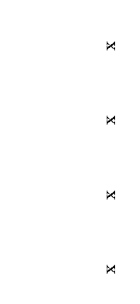 | | | x | x | x | x | | | | | | | | | | | | |
|  | | | | | | | | x | x | x | x | x | x | x | x | x | | |
|  | | | | | | | | | | | | | | | | x | x | x |

TABLE B-continued
Dye Combinations
| Structure | C12 | C13 | C14 | C15 | C16 | C17 | C18 | C19 | C20 | C21 | C22 | C23 | C24 | C25 | C26 | C27 | C28 | C29 |
|---|---|---|---|---|---|---|---|---|---|---|---|---|---|---|---|---|---|---|
|  | | | | | | | | | | | | | | | | | x | x |
|  | | | | | | | | | | | x | | | | | | | |
|  | | | | | | | | x | x | x | | | | | | | | |
|  | | x | | | | | | | | | | | | | | | | |
| 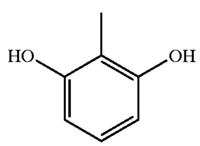 | x | | | | | | | | | | | | | | | | | |

TABLE B-continued

Dye Combinations

| Structure | C12 | C13 | C14 | C15 | C16 | C17 | C18 | C19 | C20 | C21 | C22 | C23 | C24 | C25 | C26 | C27 | C28 | C29 |
|---|---|---|---|---|---|---|---|---|---|---|---|---|---|---|---|---|---|---|
| 2-methyl-1-naphthol (OH, CH₃ on naphthalene) | | | x | | | | | | | | | x | | | | | | |
| 2-amino-4-(2-hydroxyethoxy)aniline (NH₂, OCH₂CH₂OH, NH₂) | | | | x | | | | | | | | | x | | | | | |
| 1,3-diaminobenzene (NH₂, NH₂) | | | | | x | | | | | | | | | | | | | |
| 3-aminophenol (NH₂, OH) | | | | | | x | | | | | | | | | | | | |
| 2-methyl-5-aminophenol (CH₃, OH, NH₂) | | | | | | | x | | | | | | | | | | | |
| 4,5-diamino-1-(2-hydroxyethyl)pyrazole | x | x | x | x | x | x | x | x | x | x | x | x | x | x | x | x | x | x |

TABLE C

| Structure | Dye Combinations | | | | | | | | | | | | | | | | | |
|---|---|---|---|---|---|---|---|---|---|---|---|---|---|---|---|---|---|---|
| | C30 | C31 | C32 | C33 | C34 | C35 | C36 | C37 | C38 | C39 | C40 | C41 | C42 | C43 | C44 | C45 | C46 | C47 |
| 3-aminoaniline (NH-R, NH₂) | x | x | x | x | x | x | x | x | x | x | x | x | x | x | x | x | x | x |
| 2,5-diaminotoluene | | | | | | | | | | | | | | | | | | |
| p-phenylenediamine | | | | | | | | | | | | | | | | | | |
| N-(2-hydroxyethyl)-N-(2-hydroxyethyl)-p-phenylenediamine | x | x | x | x | x | x | x | | | | | | | | | | | |
| p-aminophenol | | | | | | | | x | x | x | x | x | x | x | x | x | | |

TABLE C-continued
Dye Combinations
| Structure | C30 | C31 | C32 | C33 | C34 | C35 | C36 | C37 | C38 | C39 | C40 | C41 | C42 | C43 | C44 | C45 | C46 | C47 |
|---|---|---|---|---|---|---|---|---|---|---|---|---|---|---|---|---|---|---|
| 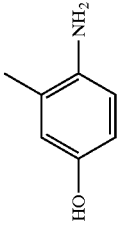 | | | | | | | | | | | | | | | | | x | x |
| 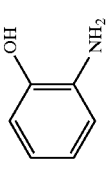 | | | | | | | x | | | | | | | | | x | | |
| 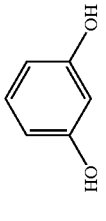 | x | | | | | | | | | | | | | | | | | x |
| 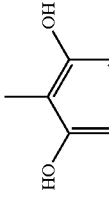 | | x | | | | | | | | | x | | | | | | | |
| 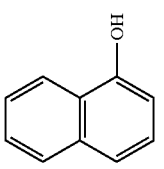 | | | | | | | | | x | x | | | | | | | | |

TABLE C-continued

Dye Combinations

| Structure | C30 | C31 | C32 | C33 | C34 | C35 | C36 | C37 | C38 | C39 | C40 | C41 | C42 | C43 | C44 | C45 | C46 | C47 |
|---|---|---|---|---|---|---|---|---|---|---|---|---|---|---|---|---|---|---|
| 2-methyl-1-naphthol |  |  | x |  |  |  |  |  |  |  |  | x |  |  |  |  |  |  |
| 2-amino-4-amino-phenol OCH₂CH₂OH ether |  |  |  | x |  |  |  |  |  |  |  |  | x |  |  |  |  |  |
| 1,3-phenylenediamine |  |  |  |  | x |  |  |  |  |  |  |  |  | x |  |  |  |  |
| 3-aminophenol |  |  |  |  |  | x |  |  |  |  |  |  |  |  | x |  |  |  |
| 2-methyl-5-aminophenol |  |  |  |  |  |  | x |  |  |  |  |  |  |  |  | x |  |  |
| 4,5-diamino-1-(2-hydroxyethyl)pyrazole | x | x |  | x | x | x | x | x | x | x | x | x | x | x | x | x | x | x |

TABLE D
| Structure | Dye Combinations | | | | | | | | | | | | | | | | | |
|---|---|---|---|---|---|---|---|---|---|---|---|---|---|---|---|---|---|---|
| | C48 | C49 | C50 | C51 | C52 | C53 | C54 | C55 | C56 | C57 | C58 | C59 | C60 | C61 | C62 | C63 | C64 | C65 |
| 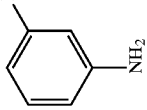 | x | x | x | x | x | x | x | x | x | x | x | x | x | x | x | x | x | x |
| 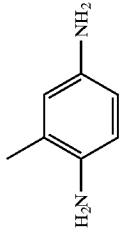 | | | | | | | | x | x | x | x | x | x | x | x | x | | |
| 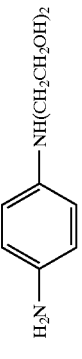 | | | | | | | | | | x | x | x | x | x | x | | x | |
| 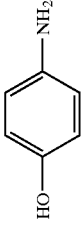 | | | | | | | | | | | | | | | | | | x |
|  | | | | | | | | x | x | x | x | x | x | x | x | x | x | x |

TABLE D-continued

| Structure | Dye Combinations | | | | | | | | | | | | | | | | | |
|---|---|---|---|---|---|---|---|---|---|---|---|---|---|---|---|---|---|---|
| | C48 | C49 | C50 | C51 | C52 | C53 | C54 | C55 | C56 | C57 | C58 | C59 | C60 | C61 | C62 | C63 | C64 | C65 |
| 4-amino-3-methylphenol (NH₂/CH₃/OH) | x | x | x | x | x | x | x | | | | | | | | | | | |
| 2-aminophenol (OH/NH₂) | | | | | | | | | | | | | | | | | x | |
| resorcinol (1,3-dihydroxybenzene) | | | | | | | | x | | | | | | | | | | x |
| 2-methylresorcinol | x | | | | | | | | x | x | | | | | | | | |
| 1-naphthol | | x | | | | | | | | | x | | | | | | | |

TABLE D-continued
Dye Combinations
| Structure | C48 | C49 | C50 | C51 | C52 | C53 | C54 | C55 | C56 | C57 | C58 | C59 | C60 | C61 | C62 | C63 | C64 | C65 |
|---|---|---|---|---|---|---|---|---|---|---|---|---|---|---|---|---|---|---|
|  |  |  | x |  |  |  |  |  |  |  |  | x |  |  |  |  |  |  |
|  |  |  |  | x |  |  |  |  |  |  |  |  | x |  |  |  |  |  |
|  |  |  |  |  | x |  |  |  |  |  |  |  |  | x |  |  |  |  |
|  |  |  |  |  |  | x |  |  |  |  |  |  |  |  | x |  |  |  |
|  |  |  |  |  |  |  | x |  |  |  |  |  |  |  |  | x |  |  |
| 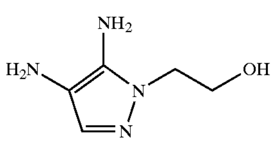 | x | x | x | x | x | x | x | x | x | x | x | x | x | x | x | x | x | x |

TABLE E

Dye Combinations

| Structure | C66 | C67 | C68 | C69 | C70 | C71 | C72 | C73 | C74 | C75 | C76 | C77 | C78 | C79 | C80 | C81 |
|---|---|---|---|---|---|---|---|---|---|---|---|---|---|---|---|---|
| m-phenylenediamine (NH-R, NH$_2$) | x | x | x | x | x | x | x | x | x | x | x | x | x | x | x | x |
| 2,4-diaminotoluene | x |   | x | x | x | x |   | x | x | x | x | x | x | x | x | x |
| p-phenylenediamine | x |   | x | x | x | x |   | x | x | x | x | x | x | x | x | x |
| N,N-bis(2-hydroxyethyl)-p-phenylenediamine |   | x | x | x | x | x |   |   |   |   |   |   |   |   |   |   |
| p-aminophenol | x |   |   |   |   |   |   |   | x | x | x | x | x | x | x | x |
| 3-amino-4-methylphenol |   |   |   |   |   |   |   | x | x | x | x | x | x | x | x | x |

TABLE E-continued

Dye Combinations

| Structure | C66 | C67 | C68 | C69 | C70 | C71 | C72 | C73 | C74 | C75 | C76 | C77 | C78 | C79 | C80 | C81 |
|---|---|---|---|---|---|---|---|---|---|---|---|---|---|---|---|---|
| 2-aminophenol (OH, NH₂) | | | | | | | | x | | | | | | | | |
| resorcinol | | | | | | | | | x | | | | | | | |
| 2-methylresorcinol | x | | | | | | | | | | | | | | | |
| 1-naphthol | | x | | | | | | | | | | | | | | |
| 2-methyl-1-naphthol | | | x | | | | | | | x | x | x | | | | |

TABLE E-continued

Dye Combinations

| Structure | C66 | C67 | C68 | C69 | C70 | C71 | C72 | C73 | C74 | C75 | C76 | C77 | C78 | C79 | C80 | C81 |
|---|---|---|---|---|---|---|---|---|---|---|---|---|---|---|---|---|
| 2-amino-4-(2-hydroxyethoxy)aniline (NH₂, OCH₂CH₂OH) | | | | x | | | | | | | | | x | | | |
| 1,3-diaminobenzene | | | | | x | | | | | | | | | x | | |
| 3-aminophenol | | | | | | x | x | | | | | | | | x | |
| 2-methyl-5-aminophenol | | | | | | | | | | | | | | | | x |
| 5-amino-1-(2-hydroxyethyl)-4-aminopyrazole | x | x | x | x | x | x | x | x | x | x | x | x | x | x | x | x |

We claim:
1. A hair dye product comprising a hair dyeing composition and a developer composition, the hair dyeing composition comprising at least one coupler of formula (1):

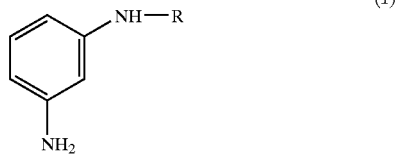

wherein R is a moiety selected from formulae (2), (3) or (4):

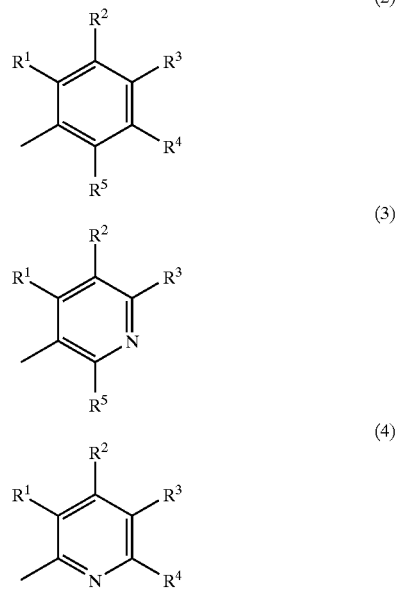

wherein $R^1$, $R^2$, $R^3$, $R^4$ and $R^5$ are each independently selected from the group consisting of a hydrogen atom, a halogen atom, a hydroxy group, an amino group, a $C_1$–$C_4$ alkyl or haloalkyl group, a $C_1$–$C_4$ alkoxy or haloalkoxy group, and a nitrile group, and at least one primary intermediate of the formula (5):

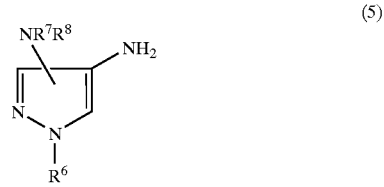

wherein $R^6$ and $R^7$ are the same or different and are selected from the group consisting of a hydrogen atom, a $C_1$ to $C_4$ alkyl group, a $C_2$ to $C_4$ hydroxyalkyl group, a benzyl group or a phenyl group, and $R^8$ is selected from the group consisting of a hydrogen atom, a $C_1$ to $C_4$ alkyl group, or a $C_2$ to $C_4$ hydroxyalkyl group, or the physiologically tolerated, water-soluble salts thereof.

2. The hair dye product according to claim 1 wherein the at least one coupler comprises a compound selected from the group consisting of N-phenyl-benzene-1,3-diamine, 4-methoxyphenyl-(3-amino-phenyl)-amine and 3-methoxyphenyl-(3-amino-phenyl)-amine and the at least one primary intermediate comprises 2-(4,5-diamino-pyrazol-1-yl)-ethanol.

3. The hair dye product according to claim 1 wherein the at least one coupler comprises a compound of formula (1) wherein R is a moiety of formula (2) and $R^1$, $R^2$, $R^3$, $R^4$ and $R^5$ are each a hydrogen atom, and the at least one primary intermediate comprises 2-(4,5-diaminopyrazol-1-yl)-ethanol.

4. A system for dyeing hair wherein at least one primary intermediate is reacted with at least one coupler in the presence of an oxidizing agent to produce an oxidative hair dye, wherein the at least one coupler comprises a compound of the formula (1):

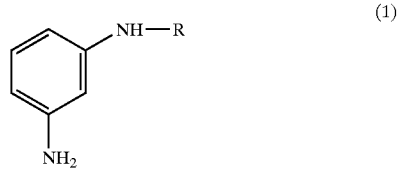

wherein R is a moiety selected from formulae (2), (3) or (4):

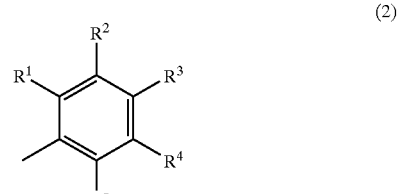

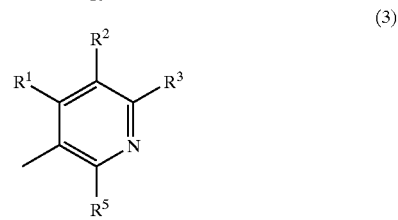

wherein $R^1$, $R^2$, $R^3$, $R^4$ and $R^5$ are each independently selected from the group consisting of a hydrogen atom, a halogen atom, a hydroxy group, an amino group, a $C_1$–$C_4$ alkyl or haloalkyl group, a $C_1$–$C_4$ alkoxy or haloalkoxy group, and a nitrile group,
and the at least one primary intermediate comprises a compound of the formula (5):

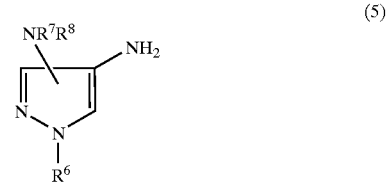

wherein $R^6$ and $R^7$ are the same or different and are selected from the group consisting of a hydrogen atom, a $C_1$ to $C_4$ alkyl group, a $C_2$ to $C_4$ hydroxyalkyl group, a benzyl group or a phenyl group, and $R^8$ is selected from the group consisting of a hydrogen atom, a $C_1$ to $C_4$ alkyl group, or a $C_2$ to $C_4$ hydroxyalkyl group, or the physiologically tolerated, water-soluble salts thereof.

5. The system for dyeing hair according to claim 4 wherein the at least one coupler comprises a compound selected from the group consisting of N-phenyl-benzene-1,3-diamine, 4-methoxyphenyl-(3-amino-phenyl)-amine and 3-methoxyphenyl-(3-amino-phenyl)-amine and the at least one primary intermediate comprises 2-(4,5-diamino-pyrazol-1-yl)-ethanol.

6. The system for dyeing hair according to claim 4 wherein the at least one coupler comprises a compound of formula (1) wherein R is a moiety of formula (2) and $R^1$, $R^2$, $R^3$, $R^4$, and $R^5$ are each a hydrogen atom, and the at least one primary intermediate comprises 2-(4,5-diaminopyrazol-1-yl)-ethanol.

7. A hair dyeing product composition for dyeing hair comprising, in a suitable carrier or vehicle, a dyeing effective amount of:

(a) at least one primary intermediate,
(b) at least one coupler; and
(c) at least one oxidizing agent;

wherein the at least one coupler comprises a coupler of formula (1):

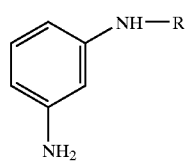

(1)

wherein R is a moiety selected from formulae (2), (3) or (4):

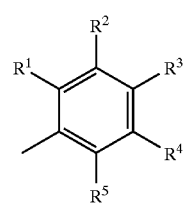

(2)

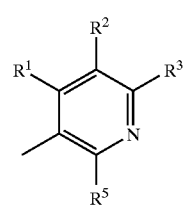

(3)

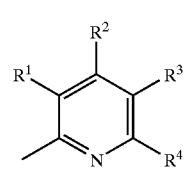

(4)

wherein $R^1$, $R^2$, $R^3$, $R^4$ and $R^5$ are each independently selected from the group consisting of a hydrogen atom, a halogen atom, a hydroxy group, an amino group, a $C_1$–$C_4$ alkyl or haloalkyl group, a $C_1$–$C_4$ alkoxy or haloalkoxy group, and a nitrile group, and the at least one primary intermediate is a compound of the formula (5):

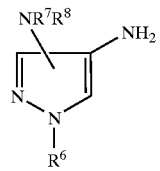

(5)

wherein $R^6$ and $R^7$ are the same or different and are selected from the group consisting of a hydrogen atom, a $C_1$ to $C_4$ alkyl group, a $C_2$ to $C_4$ hydroxyalkyl group, a benzyl group or a phenyl group, and $R^8$ is selected from the group consisting of a hydrogen atom, a $C_1$ to $C_4$ alkyl group, or a $C_2$ to $C_4$ hydroxyalkyl group, or the physiologically tolerated, water-soluble salts thereof.

8. The hair dyeing product composition of claim 7 wherein the at least one coupler comprises a compound selected from the group consisting of N-phenyl-benzene-1,3-diamine, 4-methoxyphenyl-(3-amino-phenyl)-amine and 3-methoxyphenyl-(3-amino-phenyl)-amine and the at least one primary intermediate comprises 2-(4,5-diamino-pyrazol-1-yl)-ethanol.

9. The hair dyeing product composition of claim 7 wherein the at least one coupler comprises a compound of formula (1) wherein R is a moiety of formula (2) and $R^1$, $R^2$, $R^3$, $R^4$, and $R^5$ are each a hydrogen atom, and the at least one primary intermediate comprises 2-(4,5-diaminopyrazol-1-yl)-ethanol.

10. A hair dye composition comprising, in a suitable carrier or vehicle, an effective hair dyeing amount of:

(a) at least one coupler of formula (1):

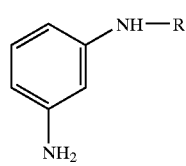

(1)

wherein R is a moiety selected from formulae (2), (3) or (4):

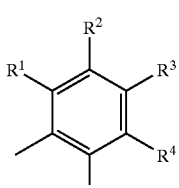

(2)

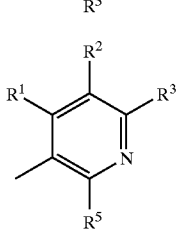

(3)

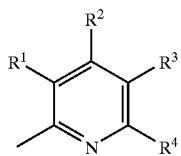

(4)

wherein $R^1$, $R^2$, $R^3$, $R^4$ and $R^5$ are each independently selected from the group consisting of a hydrogen atom, a halogen atom, a hydroxy group, an amino group, a $C_1$–$C_4$ alkyl or haloalkyl group, a $C_1$–$C_4$ alkoxy or haloalkoxy group, and a nitrile group, and (b) at least one primary intermediate of the formula (5):

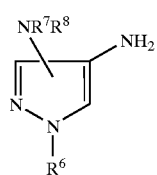

(5)

wherein $R^6$ and $R^7$ are the same or different and are selected from the group consisting of a hydrogen atom, a $C_1$ to $C_4$ alkyl group, a $C_2$ to $C_4$ hydroxyalkyl group, a benzyl group or a phenyl group, and $R^8$ is selected from the group consisting of a hydrogen atom, a $C_1$ to $C_4$ alkyl group, or a $C_2$ to $C_4$ hydroxyalkyl group, or the physiologically tolerated, water-soluble salts thereof.

11. The hair dye composition according to claim 10 wherein the at least one coupler comprises a compound selected from the group consisting of N-phenyl-benzene-1,3-diamine, 4-methoxyphenyl-(3-amino-phenyl)-amine and 3-methoxyphenyl-(3-amino-phenyl)-amine and the at least one primary intermediate comprises 2-(4,5-diaminopyrazol-1-yl)-ethanol.

12. The hair dye composition according to claim 10 wherein the at least one coupler comprises a compound of formula (1) wherein R is a moiety of formula (2) and $R^1$, $R^2$, $R^3$, $R^4$ and $R^5$ are each a hydrogen atom, and the at least one primary intermediate comprises 2-(4,5-diaminopyrazol-1-yl)-ethanol.

13. A process for dyeing hair comprising applying a dyeing effective amount of a hair dyeing product composition of claim 7 to the hair; permitting the composition to contact the hair for a period of time effective to dye the hair, and then rinsing the hair dyeing product from the hair.

14. The process according to claim 13 wherein the at least one coupler comprises a compound selected from the group consisting of N-phenyl-benzene-1,3-diamine, 4-methoxyphenyl-(3-amino-phenyl)-amine and 3-methoxyphenyl-(3-amino-phenyl)-amine and the at least one primary intermediate comprises 2-(4,5-diaminopyrazol-1-yl)-ethanol.

15. The process according to claim 13 wherein the at least one coupler comprises a compound of formula (1) wherein R is a moiety of formula (2) and $R^1$, $R^2$, $R^3$, $R^4$ and $R^5$ are each a hydrogen atom, and the at least one primary intermediate comprises 2-(4,5-diaminopyrazol-1-yl)-ethanol.

16. The process for dyeing hair comprising forming a hair dye product composition by mixing a hair dyeing composition as defined in claim 10 and a developer composition, applying to the hair an amount of the hair dye product composition effective to dye the hair, permitting the hair dye product composition to contact the hair for a period of time effective to dye the hair, and removing the hair dye product composition from the hair.

17. The process for dyeing hair according to claim 16, wherein the at least one coupler comprises a compound selected from the group consisting of N-phenyl-benzene-1,3-diamine, 4-methoxyphenyl-(3-amino-phenyl)-amine and 3-methoxyphenyl-(3-amino-phenyl)-amine and the at least one primary intermediate comprises 2-(4,5-diaminopyrazol-1-yl)-ethanol.

18. The process for dyeing hair according to claim 16, wherein the at least one coupler comprises a compound of formula (1):

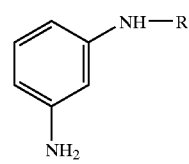

(1)

wherein R is a moiety of formula (2):
and $R^1$, $R^2$, $R^3$, $R^4$ and $R^5$ are each a hydrogen atom, and the at least one primary intermediate comprises 2-(4,5-diaminopyrazol-1-yl)-ethanol

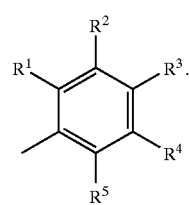

(2)

* * * * *